United States Patent [19]

Matsuno

[11] 4,079,091

[45] Mar. 14, 1978

[54] METHOD FOR THE PRODUCTION OF VINYL NORBORNENE

[75] Inventor: Mitsuo Matsuno, Kawasaki, Japan

[73] Assignee: Nippon Oil Co., Ltd., Tokyo, Japan

[21] Appl. No.: 681,901

[22] Filed: Apr. 30, 1976

Related U.S. Application Data

[63] Continuation-in-part of Ser. No. 557,324, Mar. 11, 1975, abandoned.

[51] Int. Cl.² .................... C07C 13/28; C07C 13/32
[52] U.S. Cl. .................... 260/666 PY; 260/666 B
[58] Field of Search .................... 260/666 PY, 666 B

[56] References Cited

U.S. PATENT DOCUMENTS 2,686,208   8/1954   Reed .................... 260/666 B
3,347,944   10/1967  Fritz et al. .................... 260/666 PY Primary Examiner—Veronica O'Keefe
Attorney, Agent, or Firm—Wigman & Cohen

[57] ABSTRACT

A method for producing vinyl norbornene at a high yield preventing the formation of Diels-Alder reaction by-products which is characterized in that cyclopentadiene and butadiene are reacted in the presence of p-phenylenediamine compounds such as N-isopropyl-N'-phenyl-p-phenylenediamine, N,N'-diphenyl-p-phenylenediamine and the like.

6 Claims, No Drawings

METHOD FOR THE PRODUCTION OF VINYL NORBORNENE

CROSS REFERENCE TO RELATED APPLICATION

This is a continuation-in-part application of my co-pending application, Ser. No. 557,324, filed on Mar. 11, 1975, now abandoned.

BACKGROUND OF THE INVENTION

This invention relates to a method for producing vinyl norbornene preventing the formation of by-products in Diels-Alder reaction. More particularly, the invention relates to a method for producing vinyl norbornene at a high yield preventing the formation of by-products in Diels-Alder reaction of cyclopentadiene and butadiene which is characterized in that the reaction is carried out in the presence of p-phenylenediamine compounds.

In Diels-Alder reaction, the reaction of cyclopentadiene and butadiene is brought about to produce vinyl norbornene. Since this reaction proceeds thermally, it is desirable to raise the reaction temperature to some degree, for example, 70° to 250° C. In higher temperatures, however, though some concentration of butadiene and cyclopentadiene exists, the yield of vinyl norbornene is reduced with reaction time.

One of the causes of this phenomenon is that in the literature of A. P. Plate [Zhur. Obshckei Khim., 31 131 (1961)] vinyl norbornene (I) rearranges thermally to tetrahydroindene. But the inventor has found the other one wherein vinyl norbornene is so reactive that it reacts with cyclopentadiene to produce Diels-Alder reaction by-products having 2 to 4 cyclopentadiene units and one butadiene unit as follows:

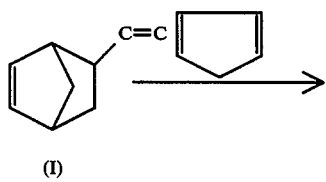

(I)

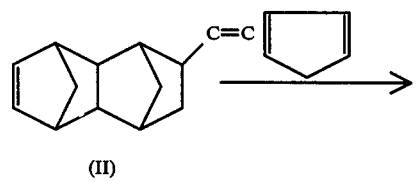

(II)

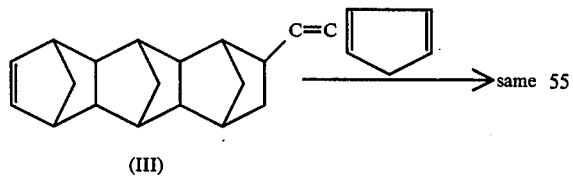

(III)

That is to say, the yield of vinyl norbornene (I) which is the object of the present invention is remarkably reduced by undesirable reactions in which cyclopentadiene is further added to vinyl norbornene (I) by a Diels-Alder reaction.

As the method for preventing the undesirable reaction at a higher temperature, those of British Pat. No. 923,462 and U.S. Pat. No. 3,201,484 are heretofore known. In the former method, organocobalt compounds are added, and in the latter method, organonickel compounds are added. While both the organocobalt and organonickel compounds are unstable in air, in addition they are weak in thermal influence, so that the use of these compounds presents many difficulties when the reaction is practically carried out.

On the other hand, it is known in U.S. Pat. No. 2,686,208 that when a cyclic compound is synthesized by using butadiene, p-phenylenediamine is added to prevent the formation of open chain polymers of butadiene. It is also known in U.S. Pat. Nos. 2,373,715 and 2,413,256 that in the case of refining and separating of butadiene, p-phenylenediamine is used as an inhibitor in order to prevent the formation of high polymers of butadiene. Further it is also known in U.S. Pat. No. 2,972,640 that p-phenylenediamine is added to preclude the formation of open chain diolefins which are a polymer of butadiene.

All of these prior patents disclose the prevention of the formation of butadiene polymers, but do nothing about the prevention of the formation of any polycyclic compound which is undesirably formed by the addition of 2-4 rings of cyclopentadiene to vinyl norbornene that is intended in the present invention.

DESCRIPTION OF THE INVENTION

As the result of eager and extensive studies of the present inventor for the purpose of overcoming the above-mentioned difficulties, it has been found that the formation of undesirable by-products of cyclopentadiene and vinyl norbornene can be suppressed or prevented by the addition of a p-phenylenediamine compound to the reaction system. Thus, the high yield of vinyl norbornene has been established.

According to the present invention, cyclopentadiene and butadiene are used as a raw material. The cyclopentadiene employed is preferably of high purity, but less than 10% by weight of any other hydrocarbon may be contained. These hydrocarbons as an impurity are preferably a saturated hydrocarbon. Further, dicyclopentadiene also may be used equivalently in the present invention. Since dicyclopentadiene is thermally decomposed in the reaction system of the present invention to form cyclopentadiene, it can be utilized on a substantial equality with cyclopentadiene.

According to the method of the present invention, cyclopentadiene and butadiene are put in a reaction vessel and heated to synthesize vinyl norbornene by Diels-Alder reaction, and at that time p-phenylenediamine compounds are added.

The p-phenylenediamine compounds used in the method of the present invention is represented by the following general formula (I):

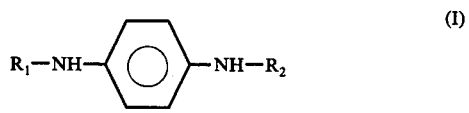

(I)

where each of $R_1$ and $R_2$ is an alkyl group, an aralkyl group, a cycloalkyl or an aryl group having carbon atom from 1 to 20, and such compounds as part of hydrogen atoms of said alkyl group, aralkyl group, cycloalkyl group or aryl group are replaced by a nitro group are included, the number of said nitro group being less than the carbon atom number of each of said hydrocarbon groups.

As the above-mentioned p-phenylenediamine compounds, there are, for example,
N,N'-diphenyl-p-phenylenediamine,
N,N'-bis(2-nitrophenyl)-p-phenylenediamine,
N-methyl-N'-phenyl-p-phenylenediamine,
N,N'-dibenzyl-p-phenylenediamine,
N-butyl-N'-phenyl-p-phenylenediamine,
N-phenyl-N'-benzyl-p-phenylenediamine,
N,N'-bis($\beta$-nitro-$\alpha$-phenylethyl)-p-phenylenediamine,
N,N'-bis-p-diphenyl-p-phenylenediamine,
N,N'-di-o-tolyl-p-phenylenediamine,
N,N'-di-$\beta$-naphthyl-p-phenylenediamine,
N-isopropyl-N'-phenyl-p-phenylenediamine,
N-butyl-N'-benzyl-p-phenylenediamine, and
N-cyclohexyl-N'-phenyl-p-phenylenediamine.

The effective quantity of these p-phenylenediamine compounds is 30 ppm to 1000 ppm, preferably 50 ppm to 500 ppm, to the total amount of cyclopentadiene and butadiene. When the amount of addition is too small, the effect of suppressing the formation of polymer becomes weak, while excess addition gives no additional effect over the proper amount only with economical disadvantage.

The molar ratio of cyclopentadiene and butadiene in the Diels-Alder reaction can be determined at any value, however, the ratio of 1:10 to 10:1 is generally preferable.

When dicyclopentadiene is employed in place of cyclopentadiene, the quantity of dicyclopentadiene is converted into that of cyclopentadiene. That is to say, one mole of dicyclopentadiene is considered to be equivalent to two moles of cyclopentadiene.

In the above reaction, inert solvents such as n-heptane, benzene and toluene; alcohols such as methanol and ethanol; and organic halides such as chlorobenzene and dichloroethane are commonly used, however, these solvents are not always necessary. Thus cyclopentadiene and butadiene can be reacted without any solvent preferably.

The reaction temperature is generally determined in the range of $-10°$ to $300°$ C, preferably $80°$ to $230°$ C. In the method of the present invention, even when the reaction temperature is raised in order to increase the reaction rate, the formation of undesirable by-products can be suppressed. Therefore, the reaction product can be obtained by the reaction in a short period of time and at a high temperature, and a high temperature reaction at $100°$ to $300°$ C can be carried out without any disadvantage. As a matter of course, the Diels-Alder reaction below $100°$ C can be safely continued for a long period of time in accordance with the method of this invention.

The reaction time may be varied in connection with the reactivities of the raw materials, for example 1 minute to 5 hours, however, it has close relation to the reaction temperature. As disclosed in the above, the formation of polymer by-product is suppressed in the method of this invention, and the reaction at a high temperature condition is possible. Therefore, the reaction can be sufficiently proceeded within a relatively short time, for example 5 to 3 hours.

The reaction pressure is not limited particularly, but in general, the reaction is performed at a pressure ranging from atmospheric pressure to 50 kg/cm$^2$.

After the completion of reaction, the product vinyl norbornene is usually separated by distillation operation.

As is illustrated later in Examples and Comparative Examples, when cyclopentadiene and butadiene are thermally reacted, by-products other than vinyl norbornene which is the object of the present invention are formed in great quantities without the addition of p-phenylenediamine compounds according to the present invention.

These by-products are separated from the reaction mixture by gas chromatography and gel permeation chromatography and are analyzed by means of infrared spectrum analysis, nuclear magnetic resonance analysis and mass spectrometry. As the result, it has been found that most of the by-products comprise various dimers other than vinyl norbornene and compounds having 2-4 cyclopentadiene rings which are formed by addition of cyclopentadiene to the product vinyl norbornene in a Diels-Alder reaction. Higher polymers of butadiene are formed only a little.

According to the method of the present invention, since the reaction is carried out in the addition of p-phenylenediamine compounds, the amount of these by-products is remarkably decreased, and vinyl norbornene can be obtained in a high yield.

The objects and features of the present invention will be further clarified by the following examples which are intended as merely illustrative and in no way restrictive of the invention.

COMPARATIVE EXAMPLE 1

In a two liter autoclave replaced with nitrogen gas inside were placed 5 moles of butadiene with a purity of 99.8% and 5 moles of cyclopentadiene with a purity of 98%, and the mixture was heated to 200° C. Reactions were carried out at the temperature for 3 hours and for 4 hours respectively. After the completion of reaction, samples of reaction liquid were taken in test tubes cooled to $-78°$ C in a dryice-methanol bath. Fractions up to trimer inclusive were analyzed by gas chromatography. Tetramers and higher polymers than tetramers were separated as a methanol-insoluble portion by pouring reaction liquid into a large excess of methanol and further were isolated by gel permeation chromatography in order to determine their quantities formed in the reaction by infrared spectrum analysis, nuclear magnetic resonance analysis and mass spectrometry. The results are shown in Table 1.

EXAMPLE 1

The reaction was carried out in the same manner as in Comparative Example 1 except that 0.3 g of N-isopropyl-N'-phenyl-p-phenylenediamine was added. The reaction product was analyzed in the same way as in Comparative Example 1. The results are also shown in Table 1.

These results clearly show that according to the method of the present invention, the product vinyl norbornene is formed at a higher yield and with a smaller amount of Diels-Alder by-products, compared with in Comparative Example 1.

Table 1

| Products | Example 1 | | Comparative Example 1 | |
|---|---|---|---|---|
| | 3 hrs | 4 hrs | 3 hrs | 4 hrs |
| Vinyl-norbornene | 31 wt% | 33 wt% | 10 wt% | 6.0 wt% |
| Dimers*[1] | 18 " | 16 " | 15 " | 14 " |
| Trimers*[2] | 26 " | 29 " | 25 " | 22 " |
| Tetramers*[3] Pentamers*[4] | 9.3 " | 12.5 " | 39 " | 49.2 " |

Table 1-continued

| Products | Example 1 3 hrs | Example 1 4 hrs | Comparative Example 1 3 hrs | Comparative Example 1 4 hrs |
|---|---|---|---|---|
| Unreacted Cyclopentadiene & Butadiene | 9.2 " | 5.3 " | 6.0 " | 4.2 " |
| Undetected | 6.5 " | 4.2 " | 5.0 " | 4.6 " |

*[1] dimers except vinylnorbornene
*[2] Diels-Alder reaction by-product having one butadiene unit and two cyclopentadiene units.
*[3] Diels-Alder reaction by-product having one butadiene unit and three cyclopentadiene units.
*[4] Diels-Alder reaction by-product having one butadiene unit and four cyclopentadiene units.

EXAMPLES 2 – 4 AND COMPARATIVE EXAMPLES 2 – 3

A mixture of butadiene (purity 99%) and dicyclopentadiene (purity 96%) in the molar ratio of 2:1 was prepared, and 120 ppm of each additive shown in the following Table 2 was added to each 480 g of this mixture. Thus formed mixture was then fed into a 2 liter stainless steel autoclave and reacted at 210° C for 3 hours. After the reaction, the reaction mixture was treated according to Example 1. The results are shown in the following Table 2.

Table 2

| Example No. | Additive | Yield of vinyl norbornene (wt%) |
|---|---|---|
| Example 2 | N-cyclohexyl-N'-phenyl-p-phenylenediamine | 35 |
| Example 3 | N,N'-diphenyl-p-phenylenediamine | 31 |
| Example 4 | N-cyclohexyl-N'-phenyl-p-phenylenediamine | 34 |
| Comparative Example 2 | Dibutyl-p-cresol | 10 |
| Comparative Example 3 | t-butyl catechol | 9.5 |

EXAMPLE 5

Another reaction was carried out under the same reaction conditions as those of Example 1, except that 100 ppm of N,N'-bis(2-nitrophenyl)-p-phenylenediamine was added and that the reaction was continued for 4 hours. As a result of analysis of the reaction product, it was found that vinyl norbornene was formed in a yield of 32% by weight.

What is claimed is:

1. In a method for producing vinyl norbornene by reacting butadiene and cyclopentadiene according to Diels-Alder reaction, the improvement comprising adding a polycyclic inhibitor to the reactants to reduce formation of polycyclic by-products normally formed during the said reaction by the addition of cyclopentadiene to vinyl norbornene and to increase the yield of vinyl norbornene to at least 30%, the reaction between butadiene and cyclopentadiene with the added polycyclic inhibitor being carried out in the absence of catalyst at a temperature of −10° to 300° C, said polycyclic inhibitor being a p-phenylenediamine compound represented by the following general formula:

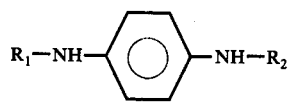

where each of $R_1$ and $R_2$ is an alkyl group, an aralkyl group, a cycloalkyl group, or an aryl group having 1 to 20 carbon atoms, and where a part of hydrogen atoms in said hydrocarbon groups may be replaced by a nitro group.

2. A method for producing vinyl norbornene as claimed in claim 1, in which said p-phenylenediamine compound is a member selected from the group consisting of:
N,N'-diphenyl-p-phenylenediamine,
N,N'-bis(2-nitrophenyl)-p-phenylenediamine,
N-methyl-N'-phenyl-p-phenylenediamine,
N,N'-dibenzyl-p-phenylenediamine,
N-butyl-N'-phenyl-p-phenylenediamine,
N-phenyl-N'-benzyl-p-phenylenediamine,
N,N'-bis(β-nitro-α-phenylethyl)-p-phenylenediamine,
N,N'-bis-p-diphenyl-p-phenylenediamine,
N,N'-di-o-tolyl-p-phenylenediamine,
N,N'-di-β-naphthyl-p-phenylenediamine,
N-isopropyl-N'-phenyl-p-phenylenediamine,
N-butyl-N'-benzyl-p-phenylenediamine, and
N-cyclohexyl-N'-phenyl-p-phenylenediamine.

3. A method for producing vinyl norbornene as claimed in claim 1, in which 30 ppm to 1000 ppm of said p-phenylenediamine compound against the total amount of said cyclopentadiene and butadiene, is used in the reaction.

4. A method for producing vinyl norbornene as claimed in claim 1, in which dicyclopentadiene is used to form cyclopentadiene in a reaction vessel in place of part of or whole of cyclopentadiene.

5. A method for producing vinyl norbornene as claimed in claim 1, in which the quantity of cyclopentadiene and butadiene to be fed to reaction is within the molar ratio of from 1:10 to 10:1.

6. A method for producing vinyl norbornene as claimed in claim 1, in which the reaction temperature is within the range of from 80° to 230° C.

* * * * *